US00PP30472P3

(12) United States Plant Patent
Dodd et al.

(10) Patent No.: US PP30,472 P3
(45) Date of Patent: May 7, 2019

(54) APPLE TREE NAMED 'MAIA-L'

(50) Latin Name: ***Malus* x *domestica***
Varietal Denomination: MAIA-L

(71) Applicant: Midwest Apple Improvement Association, Newcomerstown, OH (US)

(72) Inventors: William Dodd, Newcomerstown, OH (US); David Doud, Wabash, IN (US); John Mitchel Lynd, Pataskala, OH (US); Gregory Miller, Carrollton, OH (US)

(73) Assignee: Midwest Apple Improvement Association, Oberlin, OH (US)

( * ) Notice: Subject to any disclaimer, the term of this patent is extended or adjusted under 35 U.S.C. 154(b) by 0 days.

(21) Appl. No.: 15/731,790

(22) Filed: Jul. 31, 2017

(65) Prior Publication Data

US 2019/0037749 P1 Jan. 31, 2019

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 5/0875; A01H 5/08; A01H 5/02; A01H 6/7418
See application file for complete search history.

(56) References Cited

U.S. PATENT DOCUMENTS

PP28,545 P3 * 10/2017 Howell ..... A01H 6/7418 Plt./161

* cited by examiner

*Primary Examiner* — June Hwu
(74) *Attorney, Agent, or Firm* — Optima Law Group, APC

(57) ABSTRACT

A new and distinct variety of apple was identified from a population of seedlings derived from an open-pollinated 'Honeycrisp' block. The new variety, named 'MAIA-L' ripens late-October. 'MAIA-L' is a fast-growing, vigorous tree with large leaves. The fruit of 'MAIA-L' is a distinctive deep red color. 'MAIA-L' has consistent annual cropping with minimal horticultural inputs and is resistant to fireblight, apple scab, and powdery mildew. 'MAIA-L' fruit are large sized, extremely crisp, with complex sweet-tart flavor and long storability.

3 Drawing Sheets

Latin name: Latin name of the genus and species of the plant claimed: *Malus* x *domestica.*

Variety denomination: Variety denomination: 'MAIA-L'.

BACKGROUND OF THE INVENTION

A new and distinct variety of apple was identified from a population of seedlings derived from an open-pollinated 'Honeycrisp' (U.S. Plant Pat. No. 7,197) block. This pollination was sanctioned as a part of the Midwest Apple Improvement Association apple breeding project. 'Honeycrisp' and other select varieties were cultivated with the intention of progeny testing open-pollinated seedlings. This superior seedling tree was identified from this progeny test at Pataskala, Ohio.

The seedling tree was planted as a 1-year-old tree at Pataskala, Ohio in 2001 and grown among a population of several hundred siblings. Evaluations of fruit quality and tree growth parameters were begun in 2005 and this seedling was identified over several years as superior based upon tree growth habit, precocity, superior fruit quality, and harvest time. Utilizing grafting reproduction, the new apple tree variety was asexually propagated by Mitch Lynd in 2010 at Pataskala, Ohio and has been observed to remain true to the description set forth herein, through successive generations. While T-budding was used initially to reproduce the new apple tree variety, although it is expected that other industry recognized budding methods would be effective.

SUMMARY OF THE INVENTION

The new variety, named 'MAIA-L' is distinct from 'Honeycrisp' as 'MAIA-L' ripens late-October, 5 weeks after 'Honeycrisp' (FIG. 1). Unlike 'Honeycrisp', 'MAIA-L' is a fast-growing, vigorous tree with large leaves. The fruit of 'MAIA-L' is a distinctive deep red color (Red Group 46B to Red Group 47C). 'MAIA-L' is distinct from another Honeycrisp derived cultivar, 'MAIA-T' (U.S. Plant application Ser. No. 15/731,791), as it ripens 2 weeks before 'MAIA-T', has different coloration, and a different flavor profile. 'MAIA-L' is distinct from 'Howell TC2' (U.S. Plant Pat. No. 28,545 P3), yet another Honeycrisp derived cultivar, in that the flesh of 'Howell TC2' is red, while 'MAIA-L' is white, and they have distinct flavor profiles. 'MAIA-L' has consistent annual cropping with minimal horticultural inputs and is resistant to fireblight, apple scab, and powdery mildew. 'MAIA-L' fruit (FIG. 2) are large sized, extremely crisp, with complex sweet-tart flavor and long storability.

BRIEF DESCRIPTION OF THE DRAWINGS

The accompanying photographs show typical specimens of the new variety as depicted in color as nearly true as is reasonably possible. 'MAIA-L' photographs were taken by Diane Miller at Pataskala, Ohio.

DETAILED BOTANICAL DESCRIPTION

Figure 1:
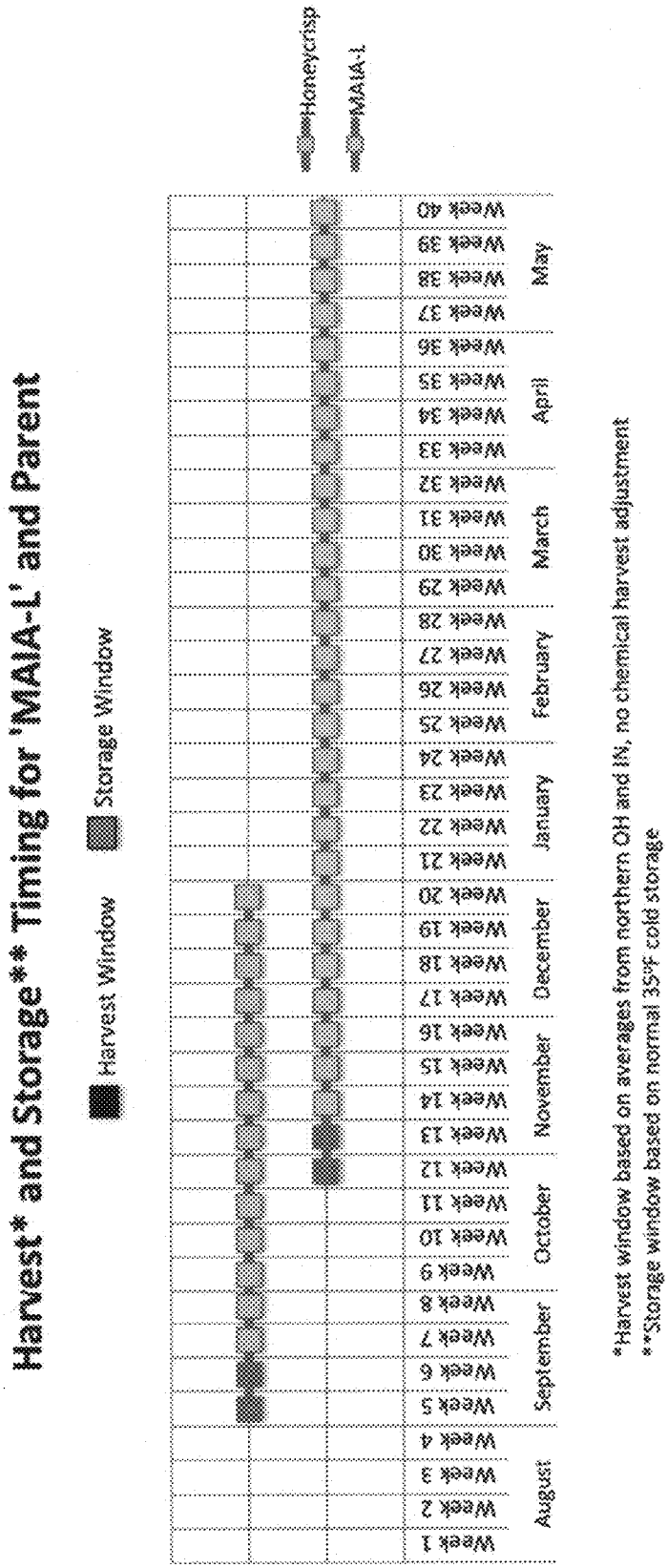
FIG. 1. A chart showing that 'MAIA-L' is distinct from 'Honeycrisp' in harvest and storage windows.
Figure 2:
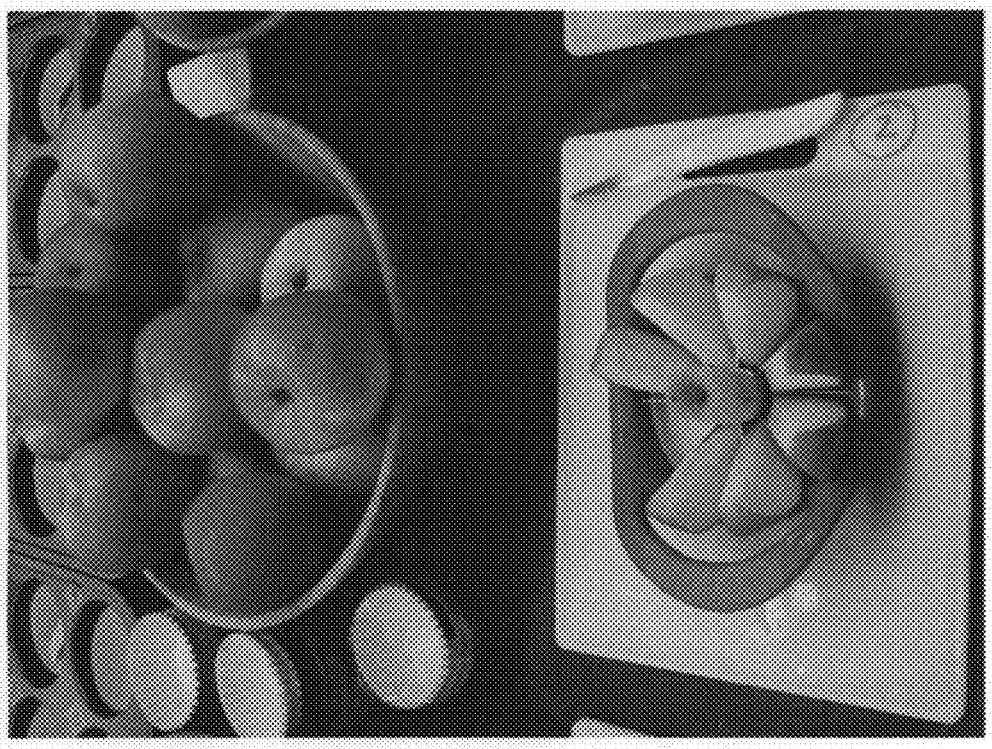
FIG. 2. An image of typical fruit of 'MAIA-L' at harvest time and sliced fruit.
Figure 3:
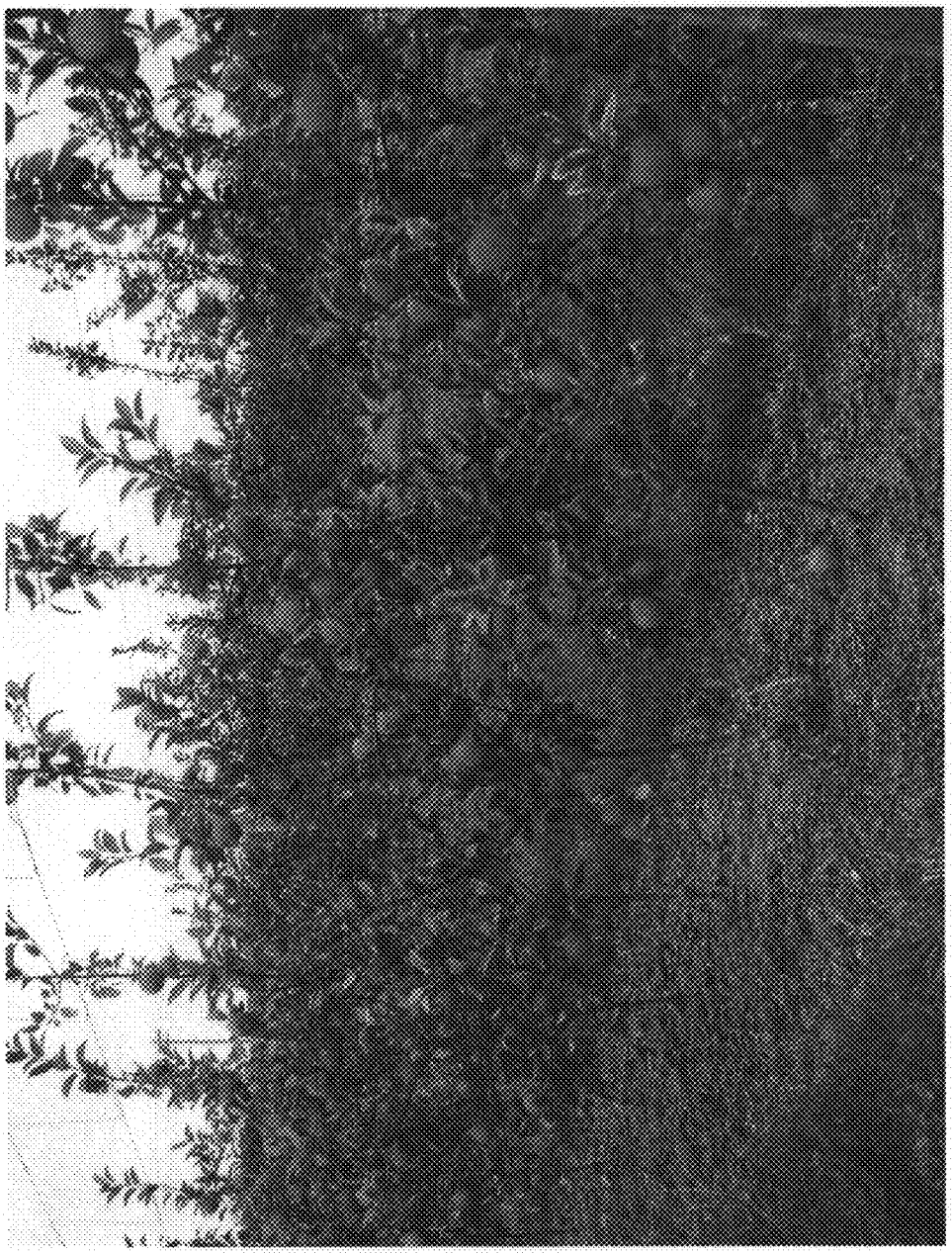
FIG. 3. An image of typical five-year-old 'MAIA-L' trees bearing fruit in October in Ohio.

Color references are made to The Royal Horticultural Society Color Chart (R.H.S.) 2001 Edition.

Parentage: 'Honeycrisp' female parent and unknown male parent; open pollination conditions cultivated by Mitch Lynd at Pataskala, Ohio in 1999.

Grafted tree on B9 rootstock (reference tree):
- *Age.*—12 years.
- *Size.*—15' height, 8' spread.
- *Vigor.*—High.
- *Form.*—Round, spreading.
- *Production.*—Very productive.
- *Growth type.*—Spindle tree growth form, productive spurs located throughout tree.
- *Bearing.*—Annual.

Trunk:
- *Reference tree diameter.*—3 cm at 15 cm height.
- *Bark color.*—Greyed-Brown 199A.
- *Lenticels.*—Oblong. 2×1 mm.
- *Lenticel color.*—Greyed-Orange 165B.
- *Lenticel density.*—5-10 lenticels/$cm^2$.

Branches:
- 3 *year old.*—10-13 mm in diameter, branch angle 80°; Greyed-Brown 199A.
- 2 *year old.*—6-8 mm in diameter, branch angle 90°; Grey-Brown N199B.
- 1 *year old.*—5-6 mm in diameter, branch angle 80°; Grey-Orange 166A.

Leaves:
- *Size.*—Length 75-117 mm; width 44-65 mm.
- *Texture.*—Leathery, crisp.
- *Form.*—Ovate.
- *Base.*—Roundly cuneate.
- *Apex.*—Acute.
- *Adaxial surface pubescence.*—None.
- *Abaxial pubescence.*—Finely pubescent.
- *Adaxial surface color.*—Green Group N137B.
- *Abaxial surface color.*—Yellow-Green 146B.
- *Veination.*—Pinnate, 6-9 major veins, mainly alternate; Yellow-Green 148D.
- *Margin.*—Serrate.
- *Petiole length.*—24-40 mm.
- *Petiole width.*—2-3 mm.
- *Petiole abaxial color.*—Yellow-Green 148D to Greyed-Purple 185B toward base and abscission layer on larger leaves.
- *Petiole groove.*—Very shallow, depth 0.1 mm.
- *Stipules.*—Present; 5 mm length; 1 mm width; Green Group N137B.
- *Leaf glands.*—None observed.

Leaf buds:
- *Length.*—3-4 mm.
- *Width.*—3-4 mm.
- *Color.*—Yellow-Green 149B with Greyed-Orange 166A overtones.
- *Placement on branch.*—Alternate.
- *Internode distance.*—30-35 mm.

Spurs: Present on 2 yr and older wood.
- *Length.*—Varies from 10 to 300 mm.
- *Relative proportion of spurs of each length.*—200-300 mm=4. 100-299 mm=4. 50-99 mm=3. 10-49 mm=6.
- *Width.*—5-8 mm.

Flowers at popcorn stage:
- *Pedicel.*—Length 12-16 mm; width 2-2.5 mm.
- *Pedicel color.*—Greyed-Green 195A.
- *Bud.*—Length 9 mm; width 6-7 mm.
- *Bud color.*—Red-Purple 58A.

Flowers at full bloom:
- *Bloom time.*—Blooms with 'Golden Delicious'.
- *Bloom period.*—Approximately 7 days.
- *Presentation.*—Very Showy.
- *Fragrance.*—Aromatic.
- *Fertility.*—Fertile.
- *Number of flowers per cluster.*—4-6 with 5 typical.

Petals:
- *Arrangement.*—Bases not overlapping; 5 petals per flower; each petal 17-20 mm length, 14-16 mm width.
- *Color.*—Upper surface (inside) White Group NN155C; Lower surface (outside) slightly colored. White Group N155B with Red-Purple 61A.
- *Shape.*—Broadly ovate, abruptly cuneate at junction with receptacle.
- *Veins.*—Distinct.
- *Margins.*—Smooth edge with notching ¾ of the way up the petal.
- *Texture.*—Soft.
- *Receptacle.*—Length 5 mm; width 3 mm; color Greyed-Purple 185C.
- *Pedicel.*—Length 10-15 mm; width 2-2.5 mm; color Greyed-Green 195A.
- *Sepals.*—5/flower; wedge-shaped, sharply pointed; length 5-6 mm; width 3 mm at widest point; color Greyed-Green 195A.
- *Stamens.*—16-20 in number.
- *Anthers.*—Length 2 mm; width 1.5 mm; color Yellow Group 8B.
- *Pollen.*—Present, color Yellow Group 10C.
- *Filaments.*—Length 7-8 mm; width 0.5 mm; color Green-White 157C.
- *Stigma.*—Held above the anthers in majority of blossoms.
- *Ovary.*—Length 3 mm; width 3 mm; color Yellow-Green 144A.
- *Style.*—Length 10 mm; styles are fused in bottom 3 mm. only; width 0.5 mm; color Yellow-Green 145B.
- *Stigma.*—Width 0.5 mm; color Yellow-Green 145B.

Pollination requirements: Requires cross-pollination from diploid varieties with overlapping bloom; will pollinate diploid varieties of overlapping bloom.

Fruit:
- *Maturity when described.*—2 month storage.
- *Date of picking.*—Oct. 20, 2016.
- *Size.*—Axial diameter 72-85 mm; Transverse diameter shortest point 37-54 mm; Transverse diameter longest point 65-80 mm.
- *Fruit weight.*—178-299 g; average 232 g.
- *Form.*—Conical, regular, symmetrical.
- *Cavity.*—Acute, medium deep, russet extends out of cavity.

*Basin*.—Medium depth, narrow, symmetrical, regular, smooth. A small amount of russet is present around the fruit basin.

*Calyx*.—Closed, small.

Skin:

*Thickness*.—Thick.

*Tendency to crack*.—None.

*Stripes*.—Light striping, medium stripe width.

*Lenticels*.—Bound shape.

*Color*.—Red Group 46B to Red Group 47C. The overcolor is dark and intense, covering a very large area of the fruit grown in full-sun.

*Ground color*.—Yellow Group 2C.

Flesh:

*Aroma*.—Sweet, very aromatic.

*Color*.—Yellow-White 158A.

*Texture*.—Crisp, firm, breaking, juicy.

*Eating quality*.—Excellent.

*Flavor*.—Sweet-tart, complex, floral.

Core: Medium size.

*Bundle area*.—1225 $mm^2$-2025 $mm^2$.

*Bundle*.—Inconspicuous.

*Axial carpel length*.—7-10 mm.

*Seed cells*.—Walls thin, tough.

Seeds:

*Number perfect*.—4-15.

*Number in one cell*.—1-3.

*Length*.—8-9 mm.

*Breadth*.—4-5 mm.

*Color*.—Greyed-Orange 177B.

Stem:

*Length*.—15-23 mm.

*Width*.—3-4 mm.

*Color*.—Greyed-Green 193B.

Use: Fresh market, dessert.

Shipping quality: Good.

Keeping quality: Good.

Drought tolerance: Average for domestic apple.

Tree winter hardiness: Average for domestic apple.

Disease:

*Resistance*.—Resistant to fireblight (*Erwinia amylovora*), apple scab (*Venturia inaequalis*), and powdery mildew (*Podosphaera leucotricha*).

*Susceptibility*.—Presumably susceptible to other fungal diseases common to *Malus domestica*.

What is claimed is:

1. A new, distinct apple tree variety named 'MAIA-L', as illustrated and described herein.

* * * * *

*Harvest window based on averages from northern OH and IN, no chemical harvest adjustment

**Storage window based on normal 35°F cold storage